United States Patent
Hanna

(10) Patent No.: US 9,633,260 B2
(45) Date of Patent: Apr. 25, 2017

(54) SYSTEM AND METHOD FOR IRIS DATA ACQUISITION FOR BIOMETRIC IDENTIFICATION

(71) Applicant: EyeLock LLC, New York, NY (US)

(72) Inventor: Keith J. Hanna, New York, NY (US)

(73) Assignee: Eyelock LLC, New York, NY (US)

( * ) Notice: Subject to any disclaimer, the term of this patent is extended or adjusted under 35 U.S.C. 154(b) by 0 days.

(21) Appl. No.: 14/946,956

(22) Filed: Nov. 20, 2015

(65) Prior Publication Data

US 2016/0148051 A1     May 26, 2016

Related U.S. Application Data

(63) Continuation of application No. 13/786,093, filed on Mar. 5, 2013, now Pat. No. 9,192,297, which is a
(Continued)

(51) Int. Cl.
*G06K 9/00* (2006.01)
*A61B 3/14* (2006.01)
(Continued)

(52) U.S. Cl.
CPC ............ *G06K 9/00604* (2013.01); *A61B 3/14* (2013.01); *G06K 9/0061* (2013.01); *G06K 9/209* (2013.01); *G06K 9/2054* (2013.01); *G06K 9/60* (2013.01)

(58) Field of Classification Search
CPC ........ A61B 3/14; G06K 9/00604; G06K 9/60; G06K 9/0021; G06K 9/00288;
(Continued)

(56) References Cited

U.S. PATENT DOCUMENTS

| 4,231,661 A | 11/1980 | Walsh et al. |
| 4,641,349 A | 2/1987 | Flom et al. |

(Continued)

FOREIGN PATENT DOCUMENTS

| KR | 10-2002-0078225 | 10/2002 |
| KR | 10-2003-0005113 | 1/2003 |

(Continued)

OTHER PUBLICATIONS

B. Galvin, et al., Recovering Motion Fields: An Evaluation of Eight Optical Flow Algorithms, Proc. of the British Machine Vision Conf. (1998).
(Continued)

*Primary Examiner* — Edward Park
(74) *Attorney, Agent, or Firm* — Foley & Lardner LLP; John D. Lanza; Paul M. H. Pua

(57) ABSTRACT

A system and related method for acquiring high quality images of the iris of an unconstrained subject comprising a camera; a controllable focusing component; a focus controller component that controls the lens to focus at successively different points within a focus range, such focus control performed without any input from measurement of whether the image is in focus or out of focus, be it based from measurements of the image or other distance metrics to the subject; and a sharpness detection component that rejects the most out-of-focus images based on measurement of focus on the image is disclosed.

18 Claims, 6 Drawing Sheets

Related U.S. Application Data continuation of application No. 12/675,189, filed as application No. PCT/US2008/074737 on Aug. 29, 2008, now Pat. No. 8,553,948.

(60) Provisional application No. 60/969,607, filed on Sep. 1, 2007.

(51) Int. Cl.
*G06K 9/60* (2006.01)
*G06K 9/20* (2006.01)

(58) Field of Classification Search
CPC .......... G06K 9/00268; G06K 9/00228; G06K 9/00261; G06K 9/00201; G06K 9/00281; G06K 9/00355; G06K 9/00597; G06K 9/0061; G06K 9/00899; G06F 3/013; G06F 21/32; G06T 2207/30041; G06T 2207/30201
See application file for complete search history.

(56) References Cited

U.S. PATENT DOCUMENTS

| | | |
|---|---|---|
| 4,910,725 A | 3/1990 | Drexler et al. |
| 4,923,263 A | 5/1990 | Johnson |
| 5,140,469 A | 8/1992 | Lamarre et al. |
| 5,259,040 A | 11/1993 | Hanna |
| 5,291,560 A | 3/1994 | Daugman |
| 5,488,675 A | 1/1996 | Hanna |
| 5,572,596 A | 11/1996 | Wildes et al. |
| 5,581,629 A | 12/1996 | Hanna et al. |
| 5,613,012 A | 3/1997 | Hoffman et al. |
| 5,615,277 A | 3/1997 | Hoffman |
| 5,737,439 A | 4/1998 | Lapsley et al. |
| 5,751,836 A | 5/1998 | Wildes et al. |
| 5,764,789 A | 6/1998 | Pare et al. |
| 5,802,199 A | 9/1998 | Pare et al. |
| 5,805,719 A | 9/1998 | Pare et al. |
| 5,838,812 A | 11/1998 | Pare et al. |
| 5,878,156 A * | 3/1999 | Okumura .............. G08B 21/06 340/575 |
| 5,901,238 A | 5/1999 | Matsushita |
| 5,953,440 A | 9/1999 | Zhang et al. |
| 5,978,494 A | 11/1999 | Zhang |
| 6,021,210 A | 2/2000 | Camus et al. |
| 6,028,949 A | 2/2000 | McKendall |
| 6,055,322 A | 4/2000 | Salganicoff et al. |
| 6,064,752 A | 5/2000 | Rozmus et al. |
| 6,069,967 A | 5/2000 | Rozmus et al. |
| 6,088,470 A | 7/2000 | Camus et al. |
| 6,144,754 A | 11/2000 | Okano et al. |
| 6,149,061 A | 11/2000 | Massieu et al. |
| 6,192,142 B1 | 2/2001 | Pare et al. |
| 6,222,903 B1 | 4/2001 | Kim et al. |
| 6,246,751 B1 | 6/2001 | Bergl et al. |
| 6,247,813 B1 | 6/2001 | Kim et al. |
| 6,252,977 B1 | 6/2001 | Salganicoff et al. |
| 6,289,113 B1 | 9/2001 | McHugh et al. |
| 6,301,375 B1 | 10/2001 | Choi |
| 6,320,610 B1 | 11/2001 | Van Sant et al. |
| 6,366,682 B1 | 4/2002 | Hoffman et al. |
| 6,373,968 B2 | 4/2002 | Okano et al. |
| 6,377,699 B1 | 4/2002 | Musgrave et al. |
| 6,424,727 B1 | 7/2002 | Musgrave et al. |
| 6,483,930 B1 | 11/2002 | Musgrave et al. |
| 6,532,298 B1 | 3/2003 | Cambier et al. |
| 6,542,624 B1 | 4/2003 | Oda |
| 6,545,810 B1 | 4/2003 | Takada et al. |
| 6,546,121 B1 | 4/2003 | Oda |
| 6,554,705 B1 | 4/2003 | Cumbers |
| 6,587,597 B1 | 7/2003 | Nakao et al. |
| 6,594,376 B2 | 7/2003 | Hoffman et al. |
| 6,594,377 B1 | 7/2003 | Kim et al. |
| 6,652,099 B2 | 11/2003 | Chae et al. |
| 6,700,998 B1 | 3/2004 | Murata |
| 6,701,029 B1 | 3/2004 | Berfanger et al. |
| 6,714,665 B1 | 3/2004 | Hanna et al. |
| 6,760,467 B1 | 7/2004 | Min et al. |
| 6,763,148 B1 | 7/2004 | Sternberg et al. |
| 6,819,219 B1 | 11/2004 | Bolle et al. |
| 6,850,631 B1 | 2/2005 | Oda et al. |
| 6,917,695 B2 | 7/2005 | Teng et al. |
| 6,920,236 B2 | 7/2005 | Prokoski |
| 6,930,707 B2 | 8/2005 | Bates et al. |
| 6,944,318 B1 | 9/2005 | Takata et al. |
| 6,950,536 B2 | 9/2005 | Houvener |
| 6,980,670 B1 | 12/2005 | Hoffman et al. |
| 6,985,608 B2 | 1/2006 | Hoffman et al. |
| 7,007,298 B1 | 2/2006 | Shinzaki et al. |
| 7,020,351 B1 | 3/2006 | Kumar et al. |
| 7,047,418 B1 | 5/2006 | Ferren et al. |
| 7,095,901 B2 | 8/2006 | Lee et al. |
| 7,106,366 B2 | 9/2006 | Parker et al. |
| 7,146,027 B2 | 12/2006 | Kim et al. |
| 7,152,782 B2 | 12/2006 | Shenker et al. |
| 7,209,271 B2 | 4/2007 | Lewis et al. |
| 7,212,330 B2 | 5/2007 | Seo et al. |
| 7,221,486 B2 | 5/2007 | Makihira et al. |
| 7,236,534 B1 | 6/2007 | Morejon et al. |
| 7,248,719 B2 | 7/2007 | Hoffman et al. |
| 7,271,939 B2 | 9/2007 | Kono |
| 7,272,265 B2 | 9/2007 | Kouri et al. |
| 7,346,472 B1 | 3/2008 | Moskowitz et al. |
| 7,385,626 B2 | 6/2008 | Aggarwal et al. |
| 7,398,925 B2 | 7/2008 | Tidwell et al. |
| 7,414,737 B2 | 8/2008 | Cottard et al. |
| 7,418,115 B2 | 8/2008 | Northcott et al. |
| 7,428,320 B2 | 9/2008 | Northcott et al. |
| 7,542,590 B1 | 6/2009 | Robinson et al. |
| 7,545,962 B2 | 6/2009 | Peirce et al. |
| 7,558,406 B1 | 7/2009 | Robinson et al. |
| 7,558,407 B2 | 7/2009 | Hoffman et al. |
| 7,574,021 B2 | 8/2009 | Matey |
| 7,583,822 B2 | 9/2009 | Guillemot et al. |
| 7,606,401 B2 | 10/2009 | Hoffman et al. |
| 7,616,788 B2 | 11/2009 | Hsieh et al. |
| 7,639,840 B2 | 12/2009 | Hanna et al. |
| 7,652,695 B2 | 1/2010 | Halpern |
| 7,660,700 B2 | 2/2010 | Moskowitz et al. |
| 7,693,307 B2 | 4/2010 | Rieul et al. |
| 7,697,786 B2 | 4/2010 | Camus et al. |
| 7,715,595 B2 | 5/2010 | Kim et al. |
| 7,719,566 B2 | 5/2010 | Guichard |
| 7,760,919 B2 | 7/2010 | Namgoong |
| 7,770,019 B2 | 8/2010 | Ferren et al. |
| 7,797,606 B2 | 9/2010 | Chabanne |
| 7,801,335 B2 | 9/2010 | Hanna et al. |
| 7,847,688 B2 | 12/2010 | Bernard et al. |
| 7,869,627 B2 | 1/2011 | Northcott et al. |
| 7,912,252 B2 | 3/2011 | Ren et al. |
| 7,916,908 B1 | 3/2011 | Thomas |
| 7,925,059 B2 | 4/2011 | Hoyos et al. |
| 7,929,017 B2 | 4/2011 | Aggarwal et al. |
| 7,929,732 B2 | 4/2011 | Bringer et al. |
| 7,949,295 B2 | 5/2011 | Kumar et al. |
| 7,949,494 B2 | 5/2011 | Moskowitz et al. |
| 7,978,883 B2 | 7/2011 | Rouh et al. |
| 8,009,876 B2 | 8/2011 | Kim et al. |
| 8,025,399 B2 | 9/2011 | Northcott et al. |
| 8,028,896 B2 | 10/2011 | Carter et al. |
| 8,090,246 B2 | 1/2012 | Jelinek |
| 8,092,021 B1 | 1/2012 | Northcott et al. |
| 8,132,912 B1 | 3/2012 | Northcott et al. |
| 8,159,328 B2 | 4/2012 | Luckhardt |
| 8,170,295 B2 | 5/2012 | Fujii et al. |
| 8,181,858 B2 | 5/2012 | Carter et al. |
| 8,195,044 B2 | 6/2012 | Hanna et al. |
| 8,212,870 B2 | 7/2012 | Hanna et al. |
| 8,214,175 B2 | 7/2012 | Moskowitz et al. |
| 8,233,680 B2 | 7/2012 | Bringer et al. |
| 8,243,133 B1 | 8/2012 | Northcott et al. |
| 8,260,008 B2 | 9/2012 | Hanna et al. |
| 8,279,042 B2 | 10/2012 | Beenau et al. |

(56) References Cited

U.S. PATENT DOCUMENTS

| | | | |
|---|---|---|---|
| 8,280,120 B2 | 10/2012 | Hoyos et al. | |
| 8,289,390 B2 | 10/2012 | Aggarwal et al. | |
| 8,306,279 B2 | 11/2012 | Hanna | |
| 8,317,325 B2 | 11/2012 | Raguin et al. | |
| 8,364,646 B2 | 1/2013 | Hanna et al. | |
| 8,411,909 B1 | 4/2013 | Zhao et al. | |
| 8,442,339 B2 | 5/2013 | Martin et al. | |
| 8,443,202 B2 | 5/2013 | White et al. | |
| 8,553,948 B2 | 10/2013 | Hanna | |
| 8,604,901 B2 | 12/2013 | Hoyos et al. | |
| 8,606,097 B2 | 12/2013 | Hanna et al. | |
| 8,719,584 B2 | 5/2014 | Mullin | |
| 2001/0028730 A1 | 10/2001 | Nahata | |
| 2002/0110286 A1 | 8/2002 | Cheatle et al. | |
| 2002/0131623 A1 | 9/2002 | Musgrave et al. | |
| 2002/0136435 A1 | 9/2002 | Prokoski | |
| 2003/0103212 A1 | 6/2003 | Westphal et al. | |
| 2003/0151674 A1 | 8/2003 | Lin | |
| 2004/0013288 A1 | 1/2004 | Svensson et al. | |
| 2004/0042643 A1 | 3/2004 | Yeh | |
| 2004/0071363 A1 | 4/2004 | Kouri et al. | |
| 2005/0084137 A1 | 4/2005 | Kim et al. | |
| 2005/0084179 A1 | 4/2005 | Hanna et al. | |
| 2005/0105778 A1 | 5/2005 | Sung et al. | |
| 2005/0168321 A1 | 8/2005 | Fitzgibbon | |
| 2005/0226471 A1 | 10/2005 | Singh et al. | |
| 2005/0264758 A1 | 12/2005 | Wakamori | |
| 2005/0270386 A1 | 12/2005 | Saitoh et al. | |
| 2005/0285943 A1 | 12/2005 | Cutler | |
| 2006/0028552 A1 | 2/2006 | Aggarwal et al. | |
| 2006/0073449 A1 | 4/2006 | Kumar et al. | |
| 2006/0074986 A1 | 4/2006 | Mallalieu et al. | |
| 2006/0097172 A1 | 5/2006 | Park | |
| 2006/0120707 A1 | 6/2006 | Kusakari et al. | |
| 2006/0170813 A1 | 8/2006 | Morofuji | |
| 2006/0188169 A1 | 8/2006 | Tener et al. | |
| 2006/0204121 A1 | 9/2006 | Bryll | |
| 2006/0279630 A1 | 12/2006 | Aggarwal et al. | |
| 2007/0040903 A1* | 2/2007 | Kawaguchi | H04N 7/15 348/14.08 |
| 2007/0098229 A1 | 5/2007 | Wu et al. | |
| 2007/0110285 A1 | 5/2007 | Hanna et al. | |
| 2007/0188613 A1 | 8/2007 | Nobori et al. | |
| 2007/0206839 A1 | 9/2007 | Hanna et al. | |
| 2007/0211922 A1 | 9/2007 | Crowley et al. | |
| 2007/0253596 A1* | 11/2007 | Murata | G06K 9/6203 382/103 |
| 2007/0286462 A1* | 12/2007 | Usher | G06K 9/0061 382/115 |
| 2007/0286524 A1 | 12/2007 | Song | |
| 2008/0031610 A1 | 2/2008 | Border et al. | |
| 2008/0075334 A1 | 3/2008 | Determan et al. | |
| 2008/0075335 A1* | 3/2008 | Martin | G06K 9/00604 382/117 |
| 2008/0089554 A1 | 4/2008 | Tabankin et al. | |
| 2008/0122578 A1 | 5/2008 | Hoyos et al. | |
| 2008/0259161 A1 | 10/2008 | Hellman et al. | |
| 2008/0291279 A1 | 11/2008 | Samarasekera et al. | |
| 2009/0047010 A1* | 2/2009 | Yoshida | G02B 7/36 396/127 |
| 2009/0074256 A1 | 3/2009 | Haddad | |
| 2009/0097715 A1 | 4/2009 | Cottard et al. | |
| 2009/0161925 A1 | 6/2009 | Cottard et al. | |
| 2009/0231096 A1 | 9/2009 | Bringer et al. | |
| 2009/0268045 A1 | 10/2009 | Sur et al. | |
| 2009/0274345 A1 | 11/2009 | Hanna et al. | |
| 2010/0014720 A1 | 1/2010 | Hoyos et al. | |
| 2010/0021016 A1 | 1/2010 | Cottard et al. | |
| 2010/0033677 A1 | 2/2010 | Jelinek | |
| 2010/0074477 A1 | 3/2010 | Fujii et al. | |
| 2010/0127826 A1 | 5/2010 | Saliba et al. | |
| 2010/0201853 A1 | 8/2010 | Ishiga | |
| 2010/0232655 A1 | 9/2010 | Hanna | |
| 2010/0238407 A1 | 9/2010 | Dai | |
| 2010/0246903 A1 | 9/2010 | Cottard | |
| 2010/0253816 A1 | 10/2010 | Hanna | |
| 2010/0278394 A1 | 11/2010 | Raguin et al. | |
| 2010/0310070 A1 | 12/2010 | Bringer et al. | |
| 2011/0002510 A1 | 1/2011 | Hanna | |
| 2011/0007949 A1 | 1/2011 | Hanna et al. | |
| 2011/0119111 A1 | 5/2011 | Hanna | |
| 2011/0119141 A1 | 5/2011 | Hoyos et al. | |
| 2011/0158486 A1 | 6/2011 | Bringer et al. | |
| 2011/0194738 A1 | 8/2011 | Choi et al. | |
| 2011/0211054 A1 | 9/2011 | Hanna et al. | |
| 2011/0277518 A1 | 11/2011 | Lais et al. | |
| 2012/0127295 A9 | 5/2012 | Hanna et al. | |
| 2012/0187838 A1 | 7/2012 | Hanna | |
| 2012/0212597 A1 | 8/2012 | Hanna | |
| 2012/0219279 A1 | 8/2012 | Hanna et al. | |
| 2012/0239458 A9 | 9/2012 | Hanna | |
| 2012/0240223 A1 | 9/2012 | Tu | |
| 2012/0242820 A1 | 9/2012 | Hanna et al. | |
| 2012/0242821 A1 | 9/2012 | Hanna et al. | |
| 2012/0243749 A1 | 9/2012 | Hanna et al. | |
| 2012/0257797 A1 | 10/2012 | Leyvand et al. | |
| 2012/0268241 A1 | 10/2012 | Hanna et al. | |
| 2012/0293643 A1 | 11/2012 | Hanna | |
| 2012/0300052 A1 | 11/2012 | Hanna et al. | |
| 2012/0300990 A1 | 11/2012 | Hanna et al. | |
| 2012/0321141 A1 | 12/2012 | Hoyos et al. | |
| 2012/0328164 A1 | 12/2012 | Hoyos et al. | |
| 2013/0051631 A1 | 2/2013 | Hanna | |
| 2013/0108125 A1 | 5/2013 | Storm et al. | |
| 2013/0110859 A1 | 5/2013 | Hanna et al. | |
| 2013/0162798 A1 | 6/2013 | Hanna et al. | |
| 2013/0162799 A1 | 6/2013 | Hanna et al. | |
| 2013/0182093 A1 | 7/2013 | Hanna | |
| 2013/0182094 A1 | 7/2013 | Hanna | |
| 2013/0182095 A1 | 7/2013 | Hanna | |
| 2013/0182913 A1 | 7/2013 | Hoyos et al. | |
| 2013/0182915 A1 | 7/2013 | Hanna | |
| 2013/0194408 A1 | 8/2013 | Hanna et al. | |
| 2013/0212655 A1 | 8/2013 | Hoyos et al. | |
| 2013/0223840 A1 | 8/2013 | Chang | |
| 2013/0294659 A1 | 11/2013 | Hanna et al. | |
| 2014/0064574 A1 | 3/2014 | Hanna et al. | |
| 2014/0072183 A1 | 3/2014 | Hanna et al. | |

FOREIGN PATENT DOCUMENTS

| | | |
|---|---|---|
| KR | 1003738500000 | 2/2003 |
| KR | 10-2003-0034258 | 5/2003 |
| KR | 10-2003-0051970 | 6/2003 |
| KR | 2003216700000 | 7/2003 |
| KR | 1004160650000 | 1/2004 |
| KR | 2003402730000 | 1/2004 |
| KR | 2003411370000 | 1/2004 |
| KR | 2003526690000 | 5/2004 |
| KR | 2003552790000 | 6/2004 |
| KR | 2003620320000 | 9/2004 |
| KR | 2003679170000 | 11/2004 |
| KR | 10-2005-0005336 | 1/2005 |
| KR | 2003838080000 | 5/2005 |
| KR | 10-2005-0051861 | 6/2005 |
| KR | 2004046500000 | 12/2005 |
| KR | 1005726260000 | 4/2006 |
| KR | 10-2009-0106791 | 10/2009 |
| KR | 10-11976780000 | 1/2012 |
| KR | 10-13667480000 | 2/2014 |
| KR | 10-2014-0028950 | 3/2014 |
| KR | 10-13740490000 | 3/2014 |
| KR | 10-2014-0039803 | 4/2014 |
| KR | 10-2014-0050501 | 4/2014 |
| WO | WO-2009/029757 A1 | 3/2009 |
| WO | WO-2009/029765 A1 | 3/2009 |
| WO | WO-2010/062371 | 6/2010 |
| WO | WO-2011/093538 | 8/2011 |

(56) References Cited

FOREIGN PATENT DOCUMENTS

| WO | WO-2012/112788 A2 | 8/2012 |
|----|-------------------|--------|
| WO | WO-2013/109295 A2 | 7/2013 |

OTHER PUBLICATIONS

Belcher et al, "A Selective Feature Information Approach for Iris Image-Quality Measure", IEEE, 3(3):572-577 (2008).
Daugman, John, "How Iris Recognition Works," IEEE Transaction on Circuits and Systems for Video Technology, 14(1):21-30 (2004).
He, Xiaofu et al., "Contactless Autofeedback Iris Capture Design", IEEE Transactions on Instrumentation and Measurement, IEEE Service Center, Piscataway, NJ, U.S. 57(7):1369-1375 (2008).
He, Y. et al, "A fast iris image quality evaluation method based on weighted entropy", SPIE, 6623:1-8 (2007).
International Preliminary Report on Patentability in PCT/US2008/074737 dated Mar. 2, 2010, 7 pages.
International Preliminary Report on Patentability in PCT/US2008/074751 dated Mar. 2, 2010, 5 pages.
International Search Report in PCT/US2008/074737, mailed Jan. 23, 2009, 4 pages.
International Search Report in PCT/US2008/074751, mailed Jan. 28, 2009, 2 pages.
J. R. Bergen, et al., Hierarchical Model-Based Motion Estimation, European Conf. on Computer Vision (1993).
K. Nishino, et al., The World in an Eye, IEEE Conf. on Pattern Recognition, vol. 1, at pp. 444-451 (Jun. 2004).
Lu, Huiqi et al., "Iris Recognition on Low Computational Power Mobile Devices", 23 pages, (2011). Retrieved from the Internet: URL: http:jjcdn.intechopen.comjpdfs-wm/14646.pdf [retrieved on Jul. 23, 2014].
Ma, L. et al, "Personal Identification Based on Iris Texture Analysis", IEEE: Pattern Analysis and Machine Intelligence, 25(12):1519-1533 (2003).
Notice of Allowance dated May 28, 2013 in U.S. Appl. No. 12/675,189.
Notice of Allowance dated Oct. 27, 2014 in U.S. Appl. No. 13/493,462.
Notice of Allowance on U.S. Appl. No. 12/658,706 dated Feb. 24, 2012.
Notice of Allowance on U.S. Appl. No. 13/493,455 dated Feb. 10, 2015.
Notice of Allowance on U.S. Appl. No. 13/493,455 dated Jul. 18, 2014.
Notice of Allowance on U.S. Appl. No. 13/786,079 dated Apr. 2, 2015.
Notice of Allowance on U.S. Appl. No. 13/786,093 dated Jul. 21, 2015.
Office Action in U.S. Appl. No. 13/398,562, mailed May 21, 2014.
Office Action on U.S. Appl. No. 12/675,189 dated Dec. 7, 2012.
Office Action on U.S. Appl. No. 13/493,455 dated Apr. 9, 2014.
Office Action on U.S. Appl. No. 13/493,455 dated Sep. 19, 2013.
Office Action on U.S. Appl. No. 13/493,462 dated Jul. 1, 2014.
Office Action on U.S. Appl. No. 13/786,079 dated Sep. 26, 2014.
Office Action on U.S. Appl. No. 13/786,093 dated Nov. 28, 2014.
Office Action on U.S. Appl. No. 13/786,102 dated Nov. 25, 2014.
Peters, Tanya H. et al., "Effects of segmentation routine and acquisition environment on iris recognition", 97 pages, (2009). Retrieved from the Internet: URL: http://etd.nd.edu/ETD-db/thesesjavailablejetd-12112009-103348/ [retrieved on Jul. 21, 2014].
R. Kumar, et al., Direct recovery of shape from multiple views: a parallax based approach, 12th IAPR Int'l Conf. on Pattern Recognition.
R. P. Wildes, Iris Recognition: An Emerging Biometric Technology, Proc. IEEE 85(9) at pp. 1348-1363 (Sep. 1997).
Written Opinion of the International Searching Authority in PCT/US2008/074737, mailed Jan. 23, 2009, 6 pages.
Written Opinion of the International Searching Authority in PCT/US2008/074751 mailed Jan. 28, 2009, 4 pages.
Office Action in U.S. Appl. No. 13/807,256, mailed Jan. 29, 2014, 16 pages.

* cited by examiner

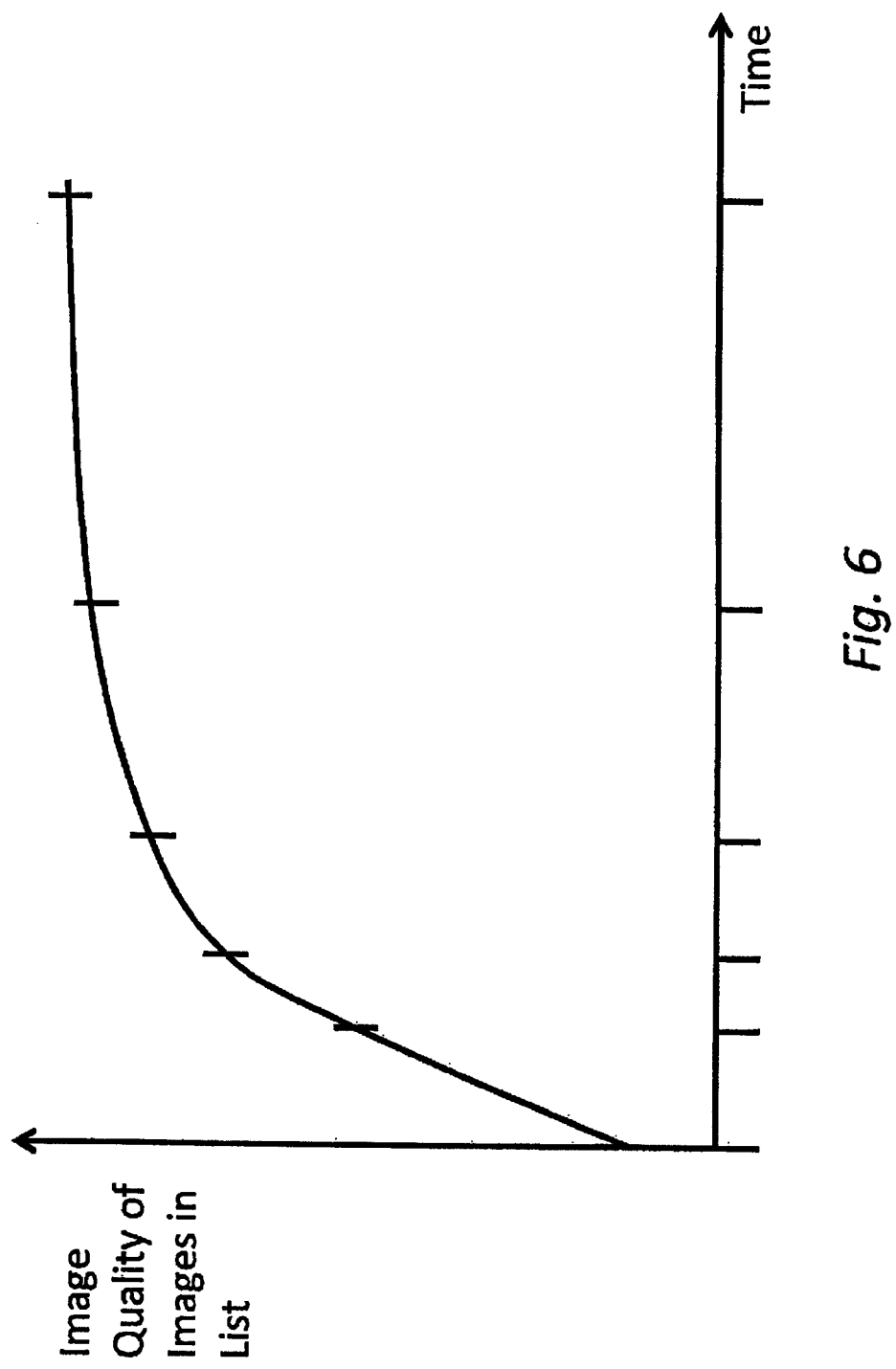

SYSTEM AND METHOD FOR IRIS DATA ACQUISITION FOR BIOMETRIC IDENTIFICATION

RELATED APPLICATIONS

This application is a continuation of and claims priority to U.S. application Ser. No. 13/786,093, entitled "SYSTEM AND METHOD FOR IRIS DATA ACQUISITION FOR BIOMETRIC IDENTIFICATION", which is a continuation of and claims priority to U.S. application Ser. No. 12/675,189, entitled "SYSTEM AND METHOD FOR IRIS DATA ACQUISITION FOR BIOMETRIC IDENTIFICATION", which is a national stage entry of International application PCT/US08/74737, filed Aug. 29, 2008, entitled "SYSTEM AND METHOD FOR IRIS DATA ACQUISITION FOR BIOMETRIC IDENTIFICATION", which claims priority to U.S. provisional application 60/969,607 filed Sep. 1, 2007, entitled "METHODOLOGY FOR ACQUIRING BIOMETRIC DATA LARGE VOLUMES", all of which are hereby incorporated by reference for all purposes.

BACKGROUND

This disclosure relates to systems and methods for acquiring biometric and other imagery, biometric acquisition, identification, fraud detection, and security systems and methods, particularly biometric systems and methods which employ iris recognition. More particularly the disclosure relates to systems and methods for acquiring iris data for iris recognition.

Iris recognition systems have been in use for some time. The acquisition of images suitable for iris recognition is inherently a challenging problem. The performance of recognition algorithms depends on the quality, i.e., sharpness and contrast, of the image of the iris of the subject who is to be identified. This is due to many reasons. As an example, the iris itself is relatively small (approximately 1 cm in diameter) and it is often required to observe it from a great distance in order to avoid constraining the position of the subject or when the subject is walking or riding. This results in a small field of view and also a small depth of field. As a second example, it is generally difficult for the adult or child subject to stay absolutely still. As a third example, the subject may blink involuntarily or drop or swivel their head momentarily to check on the whereabouts of luggage.

In biometric identification applications, due to unconstrained motion of cooperative or non-compliant subject, it has been very difficult to acquire iris images with sufficient quality for recognition and identification processing. For example, iris acquisition systems typically check whether the quality of an acquired image exceeds a threshold. Many methods of assessing quality have been developed, such as those based on a measurement of focus such as those disclosed in U.S. Pat. No. 6,753,919. The problem with this approach is that if the acquired image quality does not exceed the threshold, then the data is not acquired, despite the fact that there may never be another opportunity to acquire data from that subject again. More specifically, in the case of unconstrained users or non-cooperative subjects, it may be impossible to have the subject position themselves or wait until the acquired image data exceeds the quality threshold. For example, the subject may be distracted with their head turning in various directions, or they may be in the process of performing another task, such as boarding a bus, so that the opportunity to acquire data from them has already come and gone. More specifically, prior iris data acquisition systems have typically been designed to explicitly avoid capturing lower quality data with an emphasis on waiting or constraining the user such that only highest quality data is acquired. We have determined that even a lower quality iris image (blurred, for example) can still contain substantial evidence for matching, albeit not with the precision of a high quality iris image. However, we still wish to acquire high quality data when it is possible to do so. In another example of prior systems, for example those disclosed in U.S. Pat. No. 5,151,583, autofocus routines are used to attempt to obtain high quality iris images. However, autofocus routines cause lag times and inaccuracy, resulting in poor quality or even non-existent imaging. Other systems, such as the ones disclosed in U.S. Pat. No. 6,753,919 by Daugman, use sensors to assist a subject in aligning and focusing a hand-held video camera.

Most if not all automatic focus systems work by acquiring an image of the scene, processing the image to recover a measure of focus, using that measure of focus to move a lens-focus actuator, and then repeating the steps of image acquisition, processing and actuation many times until it is determined in the processing step that focus has been reached. In most iris recognition systems autofocus never is able to catch up with the actual position of the subject unless the subject is relatively stationary, due to the unusually low depth of field in iris recognition, as well as the requirement that the focus has to be on the iris (as opposed to the nose for example).

Because of the time delays involved in acquiring an image, processing the image, and mechanical actuation, it is impossible for auto-focus algorithms to respond instantaneously. Moreover, as the depth of field reduces, as is typically the case in iris recognition, where the object is small and is typically observed at high magnification, it becomes more difficult for auto-focus algorithms to be successful because any error in the auto-focus position is much more apparent in the imagery since the depth of field is small.

It is much more difficult for auto-focus to acquire in-focus imagery of a subject who is moving even slightly (fractions of an inch).

In the case of a person moving even slightly because there is a finite control loop time for standard auto-focus to actuate, it can be shown that if a component of the person's motion is high frequency and above the control loop response time, then the auto-focus will never be able to converge and acquire an in-focus image of the person. The auto-focus will be continually "hunting" for a focused image and will always lag the motion of the subject. The result is that the subject has to be rock solid and still when standard auto-focus is used, and this was the state of the art in iris recognition before the present invention.

Prior attempts to solve these autofocus problems use the same closed loop approach but assume a subject is moving in a straight line and then use the image measurements to try and predict where the person will be in the next frame. This approach is not very robust and also fails for random movement that subjects often have. Other auto-focus systems use different ways of computing focus measures in the scene in one or more regions to compute the most accurate focus score. When a subject is moving with frequencies that are beyond the control loop of an auto-focus algorithm auto-focus algorithms are unable to catch up to the person's motion and acquire a good image of the person.

Martin, et al., US Pat. Pub. 2008/0075335, disclose a biometric image selection method which reduces the rate of non-exploitable images which are supplied to an analysis and identification processing module using sharpness and contrast criteria. In some embodiments Martin et al. locate a pattern in each image of a sequence of images, estimate the speed of displacement of the pattern between two successive images in the sequence, and select images for which the estimated speed of displacement of the pattern is lower than a speed threshold. Martin et al. disclosed embodiments wherein two selection modules are provided, the first being a quick selection module and the second being a pupil tracking module, rejecting an image if it is below a contrast or sharpness threshold. The selection module in some embodiments selects images having the highest sharpness and/or contrast out of the images stored. Martin et al do not disclose a system or method for acquiring the series of images, nor do they disclose storing only images having higher quality than previously stored images and removing the lesser quality image from memory storage.

SUMMARY

The foregoing disadvantages and problems are overcome by the present invention which automatically acquires a series of images, analyzes the images for quality, and stores only the best quality image, not necessarily dependent on whether the quality exceeds a predetermined threshold, thereby saving memory and assuring that at least one image is stored, even if not having a quality exceeding a threshold. In a second embodiment, the system which does not require an auto-focusing system but rather automatically acquires a series of images at different focus settings regardless of the quality of images previously acquired, analyzes the images for quality, and stores only the best quality image, not necessarily dependent on whether the quality exceeds a predetermined threshold, thereby saving memory and assuring that at least one image is stored, even if not having a quality exceeding a threshold. The invention is an iris image acquisition system that, over the smallest possible time period for a particular subject, stores successively better quality images of the iris among the images acquired by the acquisition system to ensure that at least some biometric data of the subject is acquired, while at the same time accounting for arbitrary and rapid subject motion, and voluntary or involuntary subject actions such as, for example, eye blinks or head twists, all with a minimal memory requirement.

The invention is directed to acquiring iris images of optimum quality for further processing which comprises matching iris images of unknown subjects to iris image templates of known subjects. In another aspect the invention comprises a system and method of acquiring iris images having the best focus without use of autofocus systems or methods. In another aspect the invention comprises a method of acquiring iris images comprising deploying a lens with a controllable adjustable focus; and adjusting focus without feedback from a focus measurement value. In some embodiments the lens is scanned over a range of focus values. The system of the invention controls the lens to have an opportunistic capture which scans through different slices of depth volume, acquiring data. The quality of the image capture is calculated using algorithms which, for example, analyze for sharpness and or contrast, or other parameters indicative of quality and suitability for further biometric processing. The system of the invention can use algorithms looking for an absolute measure of eye focus, since an eye has some generic features in common across large populations, or for a peak in the focus measure as images are acquired over the range of focuses scanned.

BRIEF DESCRIPTION OF THE DRAWINGS

These and other objects, features, and advantages of embodiments are presented in greater detail in the following description when read in relation to the drawings, but not limited to these figures, in which:

FIG. 6 is a graphical representation of the improving quality of iris images stored in the list over time.

DETAILED DESCRIPTION

While the invention is capable of many embodiments, only a few illustrative embodiments are described below.

Figure 1:
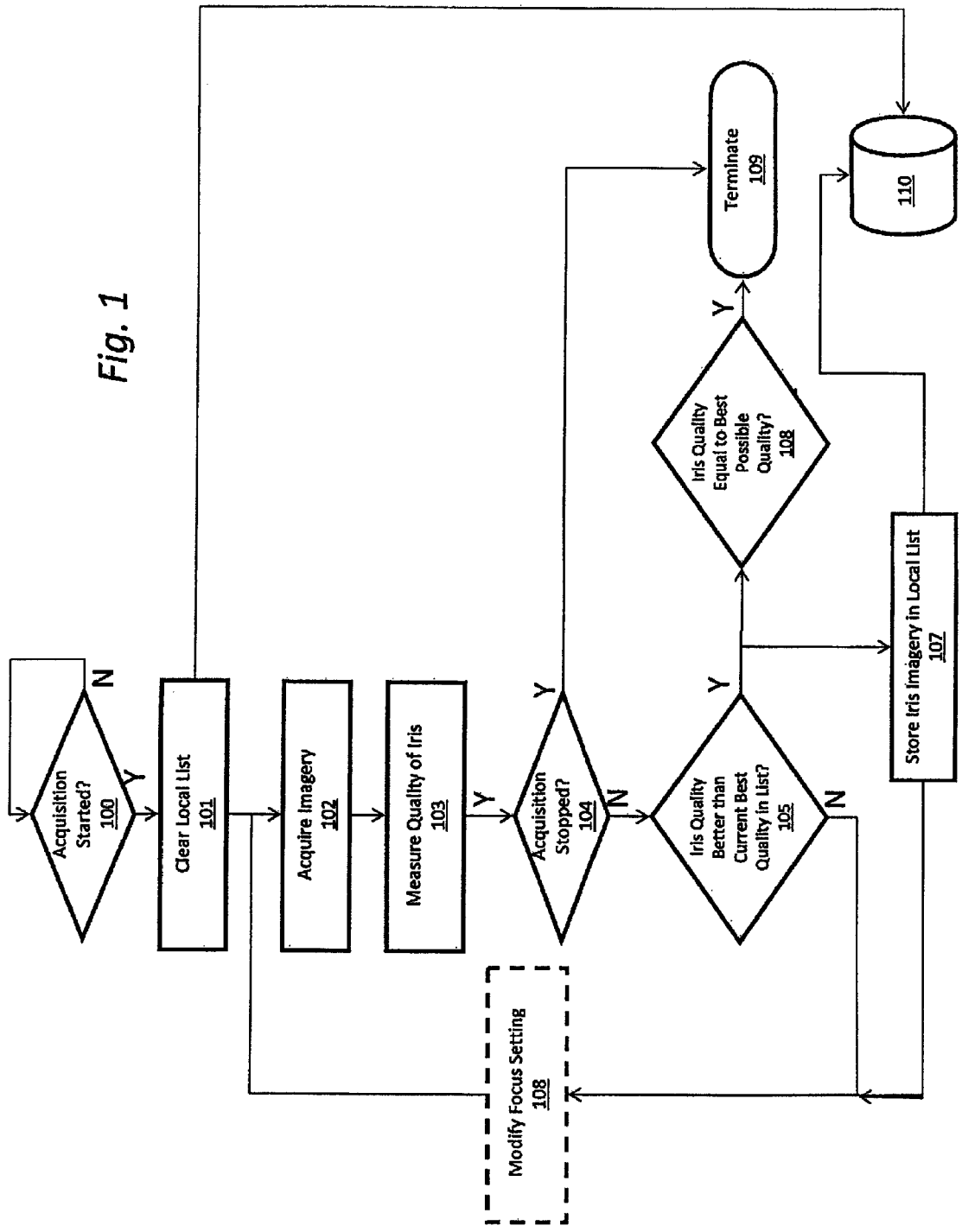
FIG. 1 is a flow chart illustrating a system of the invention.

Referring first to FIG. 1 illustrating a process flowsheet according to the invention, the process begins with a module 100 that determines whether Acquisition for a particular subject should be started. This module 100 may comprise several components depending on the specific application. For example the module may consist of a motion detector module, or a trigger that a previous subject has successfully performed a transaction with the system.

Upon initiating the acquisition, a local list of successively better images from the prior subject is cleared 101 in preparation for the next subject.

An image is then acquired 102 using a camera system. A camera system is used that can either capture images synchronously at a constant rate, or asynchronously on request by a computer-controlled trigger signal. As discussed later, the camera may be operated at a variable acquisition rate depending on the results of previous processing.

A Quality Metric module comprising, for example, one or more of the following sub-modules: face detector, eye detector, focus measurement, iris area detector is used 103 to measure the quality of each acquired image in sequence when sufficient computing capacity is available but not necessarily simultaneously with image acquisition. As discussed later, one or all of these modules may be performed at a particular time instant depending on the results of previous processing. The quality analysis and selection system of Martin et al in US 2008/0075335, supra, which is hereby incorporated by reference in its entirety, is one suitable Quality Metric system 103 for the purposes of the current invention, with the additional feature of the present invention wherein only the best or a small, limited number of the highest quality of the acquired images is stored in memory.

An Acquisition Stopped module 104 is to perform an Acquisition Stopped routine. This module 104 ensures that the overall process is not being performed unnecessarily if, for example; the subject has walked away without any data being acquired. The Acquisition Stopped module may consist of a time-out counter that compares to a threshold the difference between the current time and the time that the Acquisition process was started. The process for a particular subject can be terminated 109 or the last image can be stored 107 if a better 103 image than the best quality image stored at 110 is calculated.

A Comparator module 105 then compares the results of the Quality Metric Module with the results stored in a Local List in storage module 110. In the first iteration of the process, there will be no data in the Local List in storage module 110. However, after several iterations, some data may be present within the Local List 110. If the results of the Quality Metric Module 103 are greater than any of those on the Local List 110, then the imagery data is stored on the Local List, Storage may comprise appending the imagery data to the Local List 110, or may comprise replacing 107 imagery data on the Local List that has a lower Quality Metric 103 value.

Step 108 is optional, as indicated by the box shown with broken lines. In certain embodiments where step 108 is absent, additional imagery is acquired automatically without changing focus values but is rather acquired at a fixed focus, the quality of imagery depending on the exact location of a moving subject within the capture volume at the time successive images are acquired. In certain other embodiments when module 108 is present, the focus setting of the camera acquisition system is independently modified prior to acquiring the next image. Several methods for modifying the focus setting can be employed as discussed later.

After the focus has been modified, then imagery is once again acquired 102 in the next iteration of the process.

The process continues until 109 either the timeout condition described above occurs, or the Quality Metric 103 exceeds a value.

Figure 2:
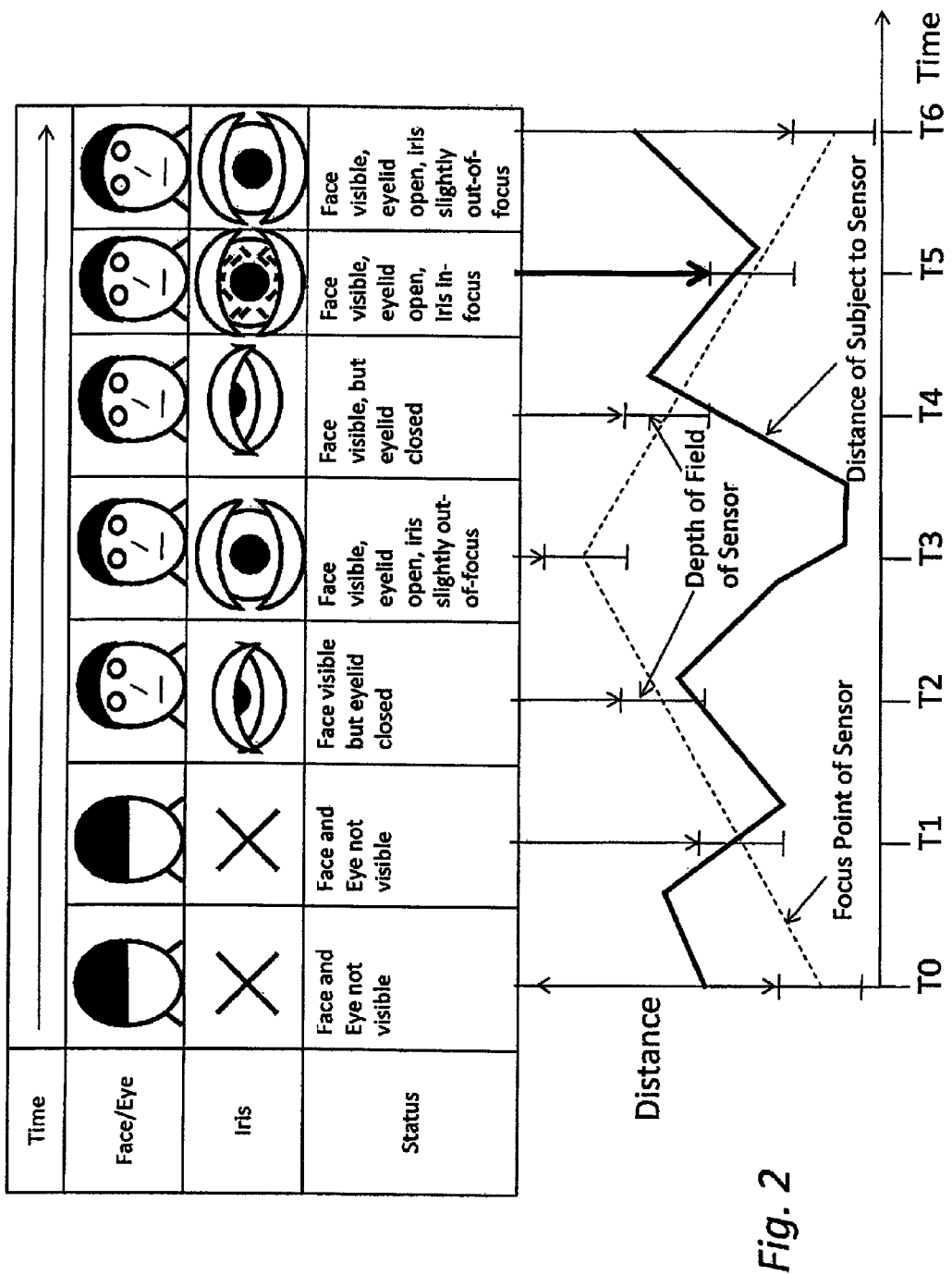
FIGS. 2-5 are graphical representations of the relationship between the focus point of a sensor, distance between a moving subject and the sensor, and a fairly constant depth of field as images T1, T2, . . . Tn are acquired over time with examples of face/eye, iris, and status at different image acquisition times Tx, each figure illustrating a different focus pattern.

Referring now to FIG. 2 the top illustration shows the disposition of an unconstrained subject over a period of time at times T0 through T6, showing that the subject may turn his head, or blink, for example. The solid, dark line in the bottom of FIG. 2 shows the disposition of the subject's distance from the camera acquisition system. Note that the subject is moving closer then further from the camera sensor in a random fashion due to their relaxed disposition or inability to remain exactly stationary. The dotted line shows the disposition of the Focus Setting position at different time instants. In this case, the Focus Setting has been set to follow a sawtooth waveform over time. The small vertical bars on the dotted line indicate the depth of field of the sensor. If the depth of the subject intersects any point within the small vertical bar, then the subject is in focus. The "Status" row at the top describes the status of the subject with respect to the image acquisition system. For example, at T=T0, the subject's head is turned and no face is visible. At T=T2, the subject's depth intersects with the depth of field of the particular focus setting at that time, however the subject's eyelid happens to be closed at that point in time. At T=T3 on the other hand, the subject's eye is present, the eye is at least partially open so that the resultant Quality Metric has a finite value, albeit a lower than optimal value since the image is slightly out of focus. The imagery at T=T3 is therefore placed on the Local List. At T=T5, the subject's eye is present, the eye is at least partially open so that the resultant Quality Metric has a finite value, and the subject's depth intersects with the depth of field of the particular focus setting at that time so that the Quality Metric has a higher value compared to that of the image that is already on the Local List, and therefore the image at T=T5 is either placed on the Local List or replaces the existing image on the Local List depending on the particular embodiment of the invention.

Figure 3:
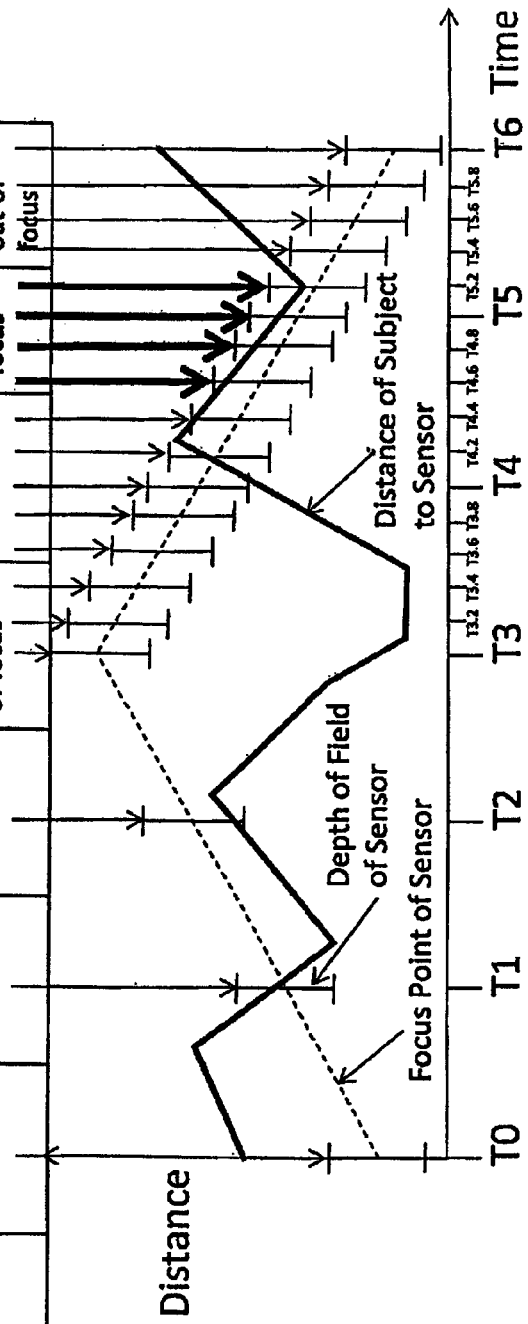

FIG. 3 shows another embodiment of the invention with a different focus setting routine. The subject's disposition is as in the previous example, but the camera acquisition module has the capability of performing rapid data acquisition over short time periods, upon certain conditions. Rapid data acquisition is not performed all the time since it is prevented by limitations in bandwidth and processing speed. In the embodiment shown in FIG. 3, the selected conditions for performing short-duration rapid data collection for a fixed time period (in this case from T=T3 to T=T6 is the detection of a face, an eye, an iris that is open, but blurred. If most of the criteria for successful acquisition have been met, then there are only very few additional criteria that need to change before valid iris data can be acquired. It is therefore more probable than at other time instants that valid iris data may soon appear. The rate of data acquisition is therefore increased in order to be ready to capture more iris data than would have otherwise been captured.

Referring now to FIG. 3, the thick vertical lines around T=T5 shows that 4 images were acquired around this time period during the rapid acquisition mode, rather than just 1 image in the prior embodiment.

Figure 4:
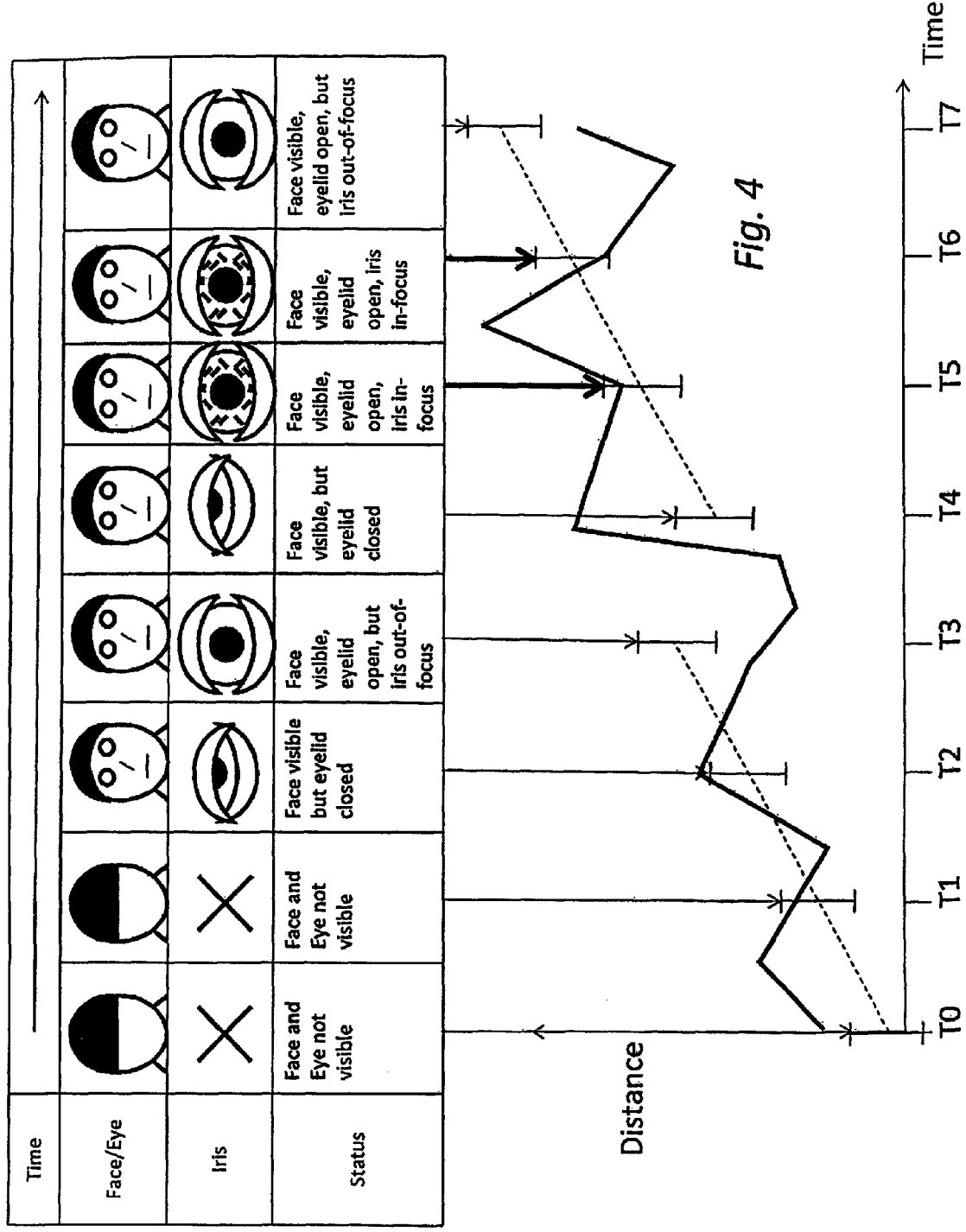
Figure 5:
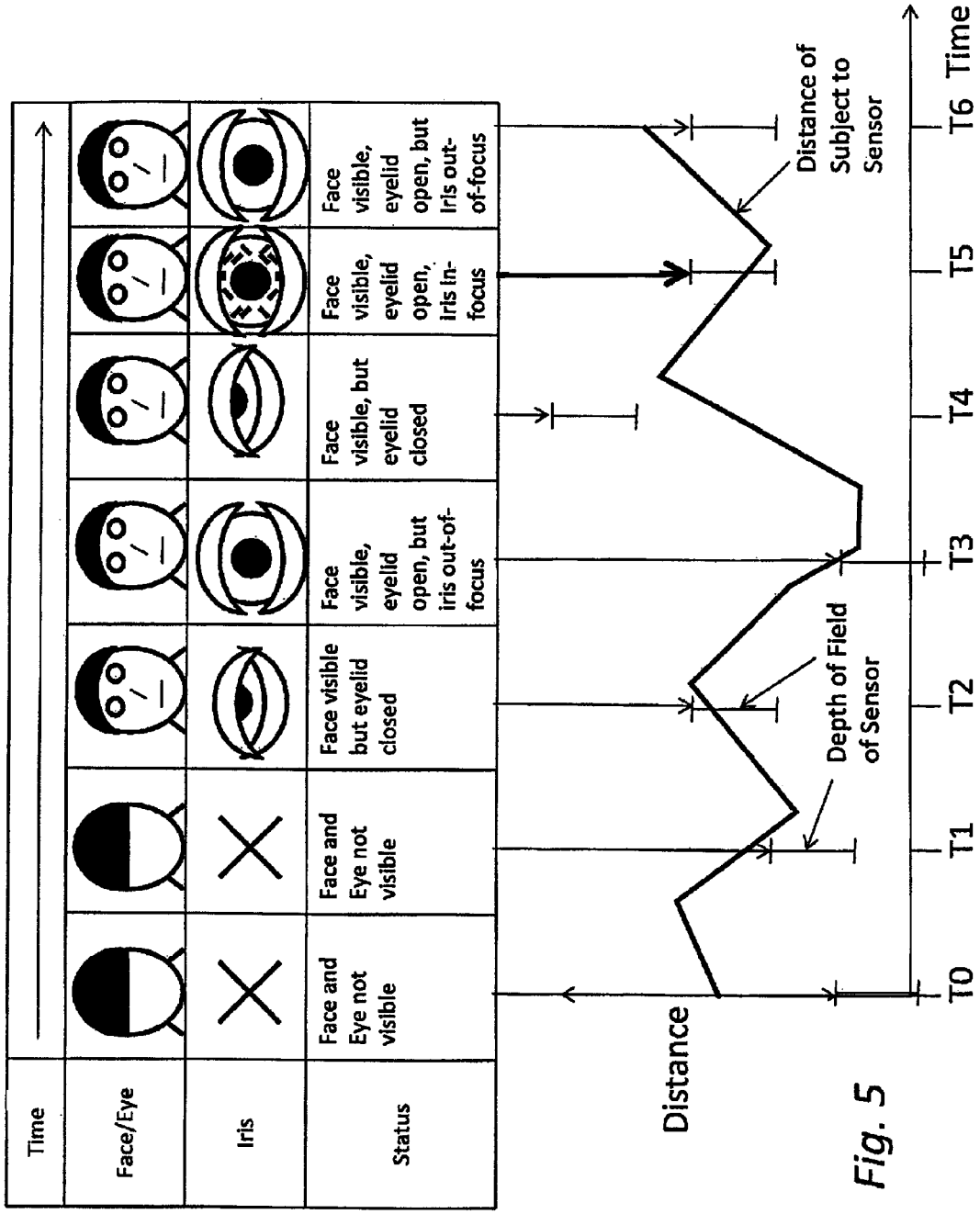

Referring to FIG. 4, the subject is moving generally towards the camera, in addition to random movement. In this case the focus setting is a combination of an auto-focus value computed from the average focus of prior settings, as well as a sawtooth waveform as described in the first embodiment. In this case, valid iris images are stored on the Local List at T=T3, T=T5 and T=T6.

FIG. 6 is a graph showing on the Y-Axis the Quality Metric value of images as they are placed on the Local List over a short time period. Typically, imagery is typically placed on the list rapidly, but then as more data is placed on the list it becomes more difficult and therefore takes longer for new imagery to exceed the existing Quality Metrics on the list. An example Quality Metric is Q=F (A+delta), where F is a focus measure where high values of F indicate more focused imagery and A is the estimated area of the iris. Various known, alternative methods for segmenting the iris and extracting the area and quantifying focus can be used.

The method is highly effective in many respects. A first advantage of the invention is if the disposition of the subject is immediately amenable to successful data acquisition (e.g. eyes are open and their face is facing the system), then the system will acquire iris imagery very rapidly. There are many methods for detecting the presence of an eye. For example, the Hough Transform disclosed in U.S. Pat. No. 3,069,654 can be configured to locate circular segments of the eye due to the iris/sclera boundary and the pupil/iris boundary.

However, if the subject is fidgeting or unable to remain stationary, or is distracted by baggage or children for example, then the acquisition system will still acquire imagery, although it might take a slightly longer period of time. However, the acquisition time for an amenable subject will not be penalized by the system's delays in acquiring data in the case of a less amenable subject. This is crucial when subject throughput is considered. This is to be contrasted with systems that may acquire and store a large number of images and then perform processing on the images to select imagery.

A second advantage of the invention is the ability to acquire successively better iris imagery. In the current art, iris image acquisition systems typically have resulted in the output of one image of the iris deemed to have a quality suitable for matching, usually exceeding a threshold. If such an image is not found, then no iris data is captured. The problem with the current art is that there are some applications when there will not be a second chance to acquire better data since the subject has gone elsewhere or is fed up with using the system. Ironically, however, the iris imagery they presented may have had plenty of information for the particular application at hand. For example, if the image acquisition system is to be used to gain entry into a house with only 100 subjects, then some of the iris imagery acquired earlier in the acquisition process may be sufficient.

A third advantage of the invention is the efficient use of memory, which is significant especially when an embedded device is used. The Local List contains only iris imagery that is successively of better quality than the prior imagery, and does not contain the imagery that was originally acquired. In addition, depending on the application, the Local List can comprise a single image which is replaced each time imagery of a better quality is detected. After processing is complete, then the resultant image remaining in the Local List is the imagery acquired of the best quality.

In one embodiment, the invention obtains in-focus images by using a focus controller component that controls the lens to focus at successively different points within a focus range, such scan control performed without any input from measurement of whether the image is in focus or out of focus, be it based from measurements of the image or other distance metrics to the subject. In terms of focus scan speed and how it relates to frame rate, exposure time these relationships and related algorithms are known to those skilled in this alt.

Even when a subject is trying to stand still, there will be residual motion. The system in some embodiments can increase or decrease the rate of image capture at different focuses in view of the degree of motion of the subject.

The system acquires a varying number of images, to account for the fact that in some cases we may acquire a good image on the first image acquisition, but in other cases may have to wait for 10 or 20 image acquisitions or more. If the system simply fixed the number of image acquisitions to be 10 or 20, then we would dramatically slow down the average time it takes to use the device, and therefore reduce the throughput of people using the device, since the number of image acquisitions acquired would be set at the worst case, rather than being adaptive based on the quality of the iris.

It is not good enough to have the focus set at the correct focal distance opportunistically since, for example, the subject may blink or turn away even though the image is in focus.

If 10 or 20 or more images are being acquired, storing them can take up a lot of memory, which can be expensive in an embedded device. The system of the invention successively checks whether the iris image quality is better than the best iris image stored previously and only in that case does the system store it. Alternatively the system can overwrite the best iris image acquired so far to replace it with the better image. In this way, the system always has the best possible iris image stored without having to use extensive memory. If the subject turns away and the system loses its opportunity to ever again acquire iris data of a subject, the best possible image, even if not of high quality, will be stored and such image may have sufficient quality for biometric identification under the circumstances.

In addition to the area to which the camera is pointed, we also can control a focus control system such that a capture volume is swept through. Unlike autofocus which requires settling time, and many discontinuous stop/start steps that eventually can wear down components and can take time to respond, we simply sweep through a focus volume rapidly, in order to opportunistically acquire biometric imagery.

While the invention has been described and illustrated in detail herein, various other embodiments, alternatives, and modifications should become apparent to those skilled in the art without departing from the spirit and scope of the invention. The claims should not be considered limited to the illustrated embodiments, therefore.

We claim:

1. A method for acquiring a series of images of an unconstrained subject, the method comprising:
   (a) acquiring, by a sensor without input from measurement of whether an image of an unconstrained subject to be acquired is in focus, the image of the unconstrained subject;
   (b) determining, based on conditions about an iris of the unconstrained subject detected in the acquired image, a time period during which there is a high probability that iris biometric data from the unconstrained subject for biometric matching is available for acquisition, the conditions about the iris comprising an estimated area of the iris that is exposed and acquired in the acquired image, and sharpness of features determined in the acquired image;
   (c) initiating acquisition of a series of images by the sensor within the determined time period, each image acquisition corresponding to a focus value within a predefined focus range, without input from measurement of whether a corresponding image to be acquired is in focus;
   (d) replacing a first image stored in a storage device, with a second image from the series of acquired images, when a quality score based on measurements of the conditions about the iris in the second image is higher than that in the first image.

2. The method of claim 1, wherein (b) further comprises detection of a feature of the subject's face or eye on the acquired image.

3. The method of claim 1, wherein (b) further comprises detection of one of: an eye or iris that is open but blurred in the acquired image, and an eye or iris that is partially open in the acquired image.

4. The method of claim 1, wherein (b) comprises determining the time period based on at least one of: a result of biometric matching using the acquired image, and detection of a physical feature or motion of the subject from the acquired image.

5. The method of claim 1, comprising configuring the sensor for operation with a single focus lens or using a single focus setting.

6. The method of claim 1, further comprising determining at least one of: a duration for the time period, an image acquisition rate, and a number of images, for the acquisition of the series of images.

7. The method of claim 1, further comprising determining, based on an estimated degree of motion of the subject, at least one of: a duration for the time period, a rate for acquisition and a number of images, for the acquisition of the series of images.

8. The method of claim 1, wherein (c) comprises acquiring the series of images at focus values according to one of a monotonic pattern, a sawtooth pattern, and a random scan pattern.

9. The method of claim 1, further comprising rejecting at least one image from the series of acquired images, based on one or more of: a result of biometric matching, measurement of image sharpness, measurement of image contrast, and detection of a feature of the subject's eye.

10. A system for acquiring a series of images of an unconstrained subject, the system comprising:
a sensor configured to acquire, without input from measurement of whether an image of an unconstrained subject to be acquired is in focus, the image of the unconstrained subject;
a controller configured to:
determine, based on conditions about an iris of the unconstrained subject detected in the acquired image, a time period during which there is a high probability that biometric data from the unconstrained subject for biometric matching is available for acquisition, the conditions about the iris comprising an estimated area of the iris that is exposed and acquired in the acquired image, and sharpness of features determined in the acquired image,
initiate acquisition of a series of images by the sensor within the determined time period, each image acquisition corresponding to a focus value within a predefined focus range, without input from measurement of whether a corresponding image to be acquired is in focus, and
replace a first image stored in a storage device with a second image from the series of acquired images, when a quality score based on measurements of the conditions about the iris in the second image is higher than that in the first image.

11. The system of claim 10, wherein the controller detects a feature of the subject's face or eye on the acquired image.

12. The system of claim 10, wherein the controller detects one of: an eye or iris that is open but blurred in the acquired image, and an eye or iris that is partially open in the acquired image.

13. The system of claim 10, wherein the controller measures at least one of sharpness and contrast of the acquired image.

14. The system of claim 10, wherein the controller determines the time period based on at least one of: a result of biometric matching using the acquired image, and detection of a physical feature or motion of the subject from the acquired image.

15. The system of claim 10, wherein the controller determines at least one of: a duration for the time period, an image acquisition rate, and a number of images, for the acquisition of the series of images.

16. The system of claim 10, wherein the controller determines, based on an estimated degree of motion of the subject, at least one of: a duration for the time period, a rate for acquisition and a number of images, for the acquisition of the series of images.

17. The system of claim 10, wherein the sensor acquires the series of images at focus values according to one of a monotonic pattern, a sawtooth pattern, and a random scan pattern.

18. The system of claim 10, wherein the controller rejects at least one image from the series of acquired images, based on one or more of: a result of biometric matching, measurement of image sharpness, measurement of image contrast, and detection of a feature of the subject's eye.

* * * * *